United States Patent [19]
Baker, Jr. et al.

[11] Patent Number: 5,974,339
[45] Date of Patent: Oct. 26, 1999

[54] HIGH ENERGY DEFIBRILLATOR EMPLOYING CURRENT CONTROL CIRCUITRY

[75] Inventors: Ross G. Baker, Jr., Houston; Pat L. Gordon, Austin, both of Tex.

[73] Assignee: Procath Corporation, West Berlin, N.J.

[21] Appl. No.: 08/979,059

[22] Filed: Nov. 26, 1997

[51] Int. Cl.$^6$ ................................ A61N 1/39
[52] U.S. Cl. ................................ 607/7
[58] Field of Search ........................ 607/4, 5, 7

[56] References Cited

U.S. PATENT DOCUMENTS

| | | |
|---|---|---|
| 3,939,844 | 2/1976 | Pequignot . |
| 4,290,430 | 9/1981 | Bihn et al. . |
| 4,295,474 | 10/1981 | Fischell . |
| 4,404,972 | 9/1983 | Gordon et al. . |
| 4,553,548 | 11/1985 | Varrichio et al. . |
| 4,566,457 | 1/1986 | Stemple . |
| 4,827,936 | 5/1989 | Pless et al. . |
| 4,866,389 | 9/1989 | Ryan et al. . |
| 4,868,908 | 9/1989 | Pless et al. . |
| 4,897,612 | 1/1990 | Carroll . |
| 4,949,719 | 8/1990 | Pless et al. . |
| 4,952,864 | 8/1990 | Pless et al. . |
| 4,964,406 | 10/1990 | Carroll et al. . |
| 4,967,747 | 11/1990 | Caroll et al. . |
| 4,969,465 | 11/1990 | Pless et al. . |
| 4,971,058 | 11/1990 | Pless et al. . |
| 4,972,835 | 11/1990 | Carroll et al. . |
| 4,989,603 | 2/1991 | Carroll et al. . |
| 5,007,422 | 4/1991 | Pless et al. . |
| 5,014,697 | 5/1991 | Pless et al. . |
| 5,014,701 | 5/1991 | Pless et al. . |
| 5,025,172 | 6/1991 | Carroll et al. . |
| 5,027,814 | 7/1991 | Carroll et al. . |
| 5,048,521 | 9/1991 | Pless et al. . |
| 5,111,816 | 5/1992 | Pless et al. . |
| 5,115,807 | 5/1992 | Pless et al. . |
| 5,127,421 | 7/1992 | Bush et al. . |
| 5,130,571 | 7/1992 | Carroll . |
| 5,131,388 | 7/1992 | Pless et al. . |
| 5,163,428 | 11/1992 | Pless . |
| 5,176,135 | 1/1993 | Fain et al. . |
| 5,222,492 | 6/1993 | Morgan et al. . |
| 5,249,573 | 10/1993 | Fincke et al. . |
| 5,336,253 | 8/1994 | Gordon et al. . |
| 5,342,404 | 8/1994 | Alt et al. . |
| 5,397,336 | 3/1995 | Hirschberg et al. ............ 607/6 |
| 5,403,351 | 4/1995 | Saksena . |
| 5,403,355 | 4/1995 | Alt . |
| 5,405,361 | 4/1995 | Persson . |
| 5,411,527 | 5/1995 | Alt . |
| 5,431,685 | 7/1995 | Alt . |
| 5,443,490 | 8/1995 | Flugstad . |
| 5,470,341 | 11/1995 | Kuehn et al. . |
| 5,529,579 | 6/1996 | Alt et al. . |
| 5,545,182 | 8/1996 | Stotts et al. . |
| 5,571,159 | 11/1996 | Alt . |
| 5,591,209 | 1/1997 | Kroll . |
| 5,607,454 | 3/1997 | Cameron et al. . |
| 5,645,572 | 7/1997 | Kroll et al. . |
| 5,658,319 | 8/1997 | Kroll . |
| 5,725,560 | 3/1998 | Brink ................................ 607/5 |

OTHER PUBLICATIONS

Schuder, John C.; Stoeckle, Harry; West, James K.; Dolan, Alfred M., "A Very High Power Amplifier for Experimental External Defibrillation," 16th Annual Conference on Engineering in Medicine and Biology; May 1963.

Schuder, John C.; Rahmoeller, Glenn A.; Stoeckle, Harry, "Transthoracic Ventricular Defibrillation with Triangular and Trapezoidal Waveforms," Circulation Research, vol. XIX, Oct. 1964.

*Primary Examiner*—Jeffrey R. Jastrzab
*Attorney, Agent, or Firm*—Fitch, Even, Tabin & Flannery

[57] ABSTRACT

A defibrillator for providing a constant low pulsed current to a patient's heart has a high voltage capacitor for storing electrical energy. An inductor connected to the capacitor smooths out the discharge curve and produces a low current low frequency defibrillator pulse supplied to a patient's heart. The pulse is usually biphasic.

21 Claims, 16 Drawing Sheets

HIGH ENERGY DEFIBRILLATOR EMPLOYING CURRENT CONTROL CIRCUITRY

BACKGROUND OF THE INVENTION

The invention relates in general to a defibrillator and in particular, to a defibrillator for supplying a high energy pulse at a relatively low steady current to avoid causing discomfort to a patient to whom the defibrillator pulse is supplied while providing effective atrial defibrillation.

Cardiac defibrillators are used to provide a high energy electric pulse from a high voltage capacitor to a patient's heart for the purpose of restoring normal sinus rhythm. In some cases, persons who have previously had myocardial infarctions may be prone to ventricular or atrial tachycardia, unwanted racing of one or more chambers of the heart. Such tachycardia may lead to fibrillation of the myocardium usually of the ventricle. Fibrillation is the random firing of the muscle fibers of the myocardium. The random firing prevents the uniform pulsatile contraction normally associated with pumping of the heart. When fibrillation occurs all effective pumping stops, The normal sinus rhythm must be restored within a few minutes in order to prevent damage to tissues needing large amounts of oxygen such as the brain. Failure to restore normal sinus rhythm leads to death.

Paddle-type defibrillators typically provide up to 400 joules of electrical energy through the surface of the chest and into the heart to restore the normal sinus rhythm. Typically the discharge of current leads to a "resetting" of the electrical condition of the heart cells. The cells can then depolarize in a depolarization wave traveling along the heart. The depolarization wave causes the uniform pumping contraction of the heart characteristic of normal sinus rhythm.

However, it is also known that discharging that amount of electrical energy into the body of a patient is extremely painful and can cause the patient great discomfort. Normally, however, the patient in ventricular fibrillation has already lost consciousness and does not experience pain.

It is also known that although some patients do not have problems with ventricular fibrillation, particularly the elderly, they may suffer from atrial fibrillation. Unlike ventricular fibrillation which leads to total loss of the cardiac pumping function, atrial fibrillation, while not immediately life-threatening may nevertheless be dangerous. Atrial fibrillation causes a loss in the pumping capacity of the atriums which deliver blood to the ventricles. In particular, in atrial fibrillation a portion of the blood volume, which is normally ejected from the atriums into the ventricles, will remain behind. This can lead to stagnation of the blood within the atriums and increase the risk of the formation of a thrombus or a release of an embolus. Such emboli may be pumped out of the atrium through the ventricle and out into the generalized circulation of the body. The embolus may lodge in the brain causing a cerebrovascular accident or stroke. It may cause phlebitis if it lodges in one of the limbs such as the legs. If the embolus is generated in the right atrium, it may be carried into the circulatory system of the lungs leading to a pulmonary embolism. While none of the these conditions other than stroke, are immediately life threatening, once the embolus travels and lodges the eventual damage can be extremely debilitating or even ultimately fatal.

It is presently known that in order to provide cardioversion or the restoration of normal rhythm to an atrium, this may be accomplished by the introduction of a catheter, such as a Swan-Ganz catheter, into the brachial artery of the arm. The catheter is then passed through the pulmonary artery into one of the right atrium of the heart. While the patient is normally unconscious or heavily sedated in situations where ventricular cardioversion is to take place, and time is of the essence, patients are often not so heavily sedated or are unconscious for atrial cardioversion. As a result, the normal discharge of electrical energy through the heart for atrial cardioversion can be disconcerting and in some cases painful. One reason why the atrial cardioversion current can be painful is because a typical capacitive discharge starts at a very high current and then decays exponentially with time to a low current. The large magnitude of the current at the onset tends to cause pain in and of itself. In addition, at the beginning of the exponentially-decaying current discharge the time rate of change of the current is very large. This tends to be at a rate which directly stimulates pain nerves associated with the heart and adds additional pain.

It is also known from physiological studies that the rapidly changing high onset current, which often results in the pain, is not particularly effective for atrial cardioversion. Rather, it is the total current over the exponential curve that is required to be at a minimum level in order to achieve cardioversion. Typically, for instance, five to ten joules can be used for atrial cardioversion. Thirty joules would have to be delivered to the heart for ventricular cardioversion.

Some workers in the art may have partially solved these problems by providing defibrillators having high voltage discharge capacitors that supply defibrillating current to inductors for later delivery to the patient. As discussed in U.S. Pat. No. 4,566,457 to Stemple, U.S. Pat. No. 5,249,573 to Fincke et al., U.S. Pat. No. 5,443,490 to Flugstad, U.S. Pat. No. 5,591,209 to Kroll and U.S. Pat. No. 5,607,454 to Cameron et al., the inductors are used for pulse shaping. Cameron et al. cite Anderson et al., "The Efficacy of Trapezoidal Wave Forms for Ventricular Defibrillation," *Chest,* 70(2):298–300 (1976) which discloses that trapezoidal waveform current pulses may be used for defibrillation. The use of triangular and trapezoidal waveforms for defibrillation is also disclosed in Schuder, J. C., Rahmoeller, G. A., and Stoeckle, H., "Transthoracic Ventricular Defibrillation with Triangular and Trapezoidal Waveforms," *Circulation Research,* vol. XIX, pp. 689–694, October 1966. Schuder et al. cite Schuder, J. C., Stoeckle, H., West, J. K. and Dolan, A. M., "A Very High Power Amplifier for Experimental External Defibrillation," 16th Annual Conference on Engineering in Medicine and Biology, p. 40, (1963).

A switching defibrillation system is disclosed in U.S. Pat. No. 5,222,492 to Morgan et al. The Morgan et al. system includes a capacitor coupled by a series-connected field effect transistor switch connected to an inductor. The transistor is switched multiple times during a defibrillation pulse for the purpose of providing the pulse with a sinusoidal shape. A control circuit receives feedback representative of the defibrillation pulse and controls the pulse shape by controlling the pulse widths into a gate of the field effect transistor.

What is needed then is a way of supplying a uniform current without the high onset current and high time rate of change of current produced by present atrial defibrillators.

SUMMARY OF THE INVENTION

The present invention relates to a low current, relatively low frequency defibrillator for use in atrial defibrillation in a patient. The system provides, via a capacitor, a relatively large amount of electrical energy. However, the defibrillating current is supplied as a relatively steady current pulse.

The voltage available for providing electromotive force from the capacitor. The capacitor voltage drives a current through an inductor which removes a portion of the high frequency components from the exponential current the capacitor. A control circuit including a microcontroller connects and disconnects a patient circuit, including a Swan-Ganz catheter, via the inductor at a high rate. This provides a relatively steady current through the patient circuit of about 5 amperes. Although a slight sawtooth is presented due to the toggling of the atrial defibrillation current, the defibrillator embodying the present invention avoids pain being generated in the patient by only supplying relatively low frequency defibrillating current. The apparatus also avoids discomfort to the patient by supplying a relatively steady but low amplitude current of about 5 amperes which does not have high frequency components that stimulate pain nerves.

The apparatus achieves this by using a charge storage device in combination with an inductor under the active control of the switching circuit in combination with a microcontroller. The switch toggles between ground and the high voltage terminal of the capacitor to provide a pulsed current to the inductor which smooths the output defibrillation pulse. The present switching arrangement, by toggling between the high voltage side and ground, provides an output with less unwanted current variation than the prior art systems such as Morgan et al. This in turn reduces the likelihood that the nervous system will be stimulated by the defibrillation pulse leading to pain.

It is a principal object of the present invention to provide a defibrillator system having relatively low frequency current.

It is another object of the present invention to provide a defibrillator system having a relatively low steady current but providing sufficient energy to defibrillate a patient.

It is still another object of the present invention to provide a low current defibrillator for the production of a biphasic or multiphasic current waveform to a patient.

DETAILED DESCRIPTION OF THE PREFERRED EMBODIMENT

Figure 1:
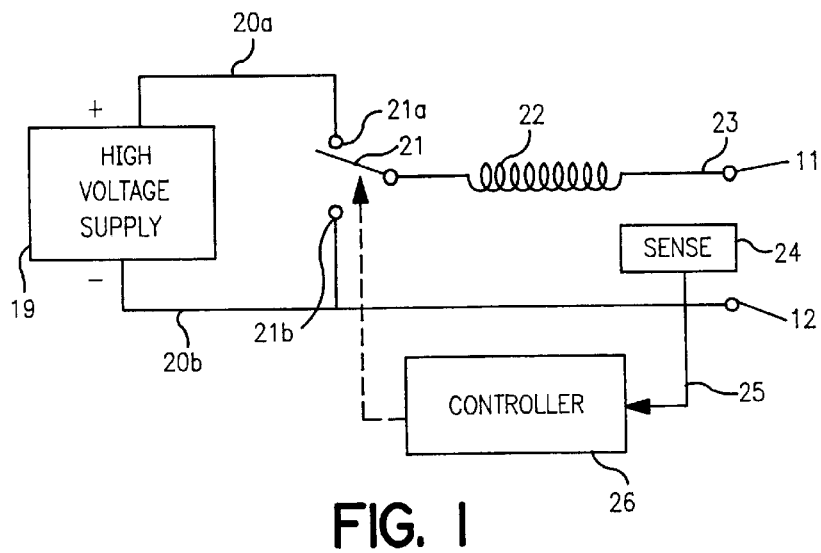
FIG. 1 is a schematic diagram of a defibrillator embodying the present invention.

Referring now to the drawings, and especially FIGS. 1 through 4, a multiphasic current-controlled defibrillator, generally identified by reference numeral 10, is shown therein. The defibrillator 10 is for cardioversion of atrial fibrillation and may be used for ventricular defibrillation as well. It is intended to deliver high energy pulse stimulation to a patient's heart through a pair of catheter electrodes 11 and 12 of a Swan-Ganz catheter 13. The catheter electrodes are placed directly in contact with heart tissue 14 of a heart 15 of a patient 16. The catheter electrodes 11 and 12 can contact the heart tissue 14 in such a way as to deliver high energy pulse stimulation either to an atrium 17 or a ventricle 18.

Figure 2:
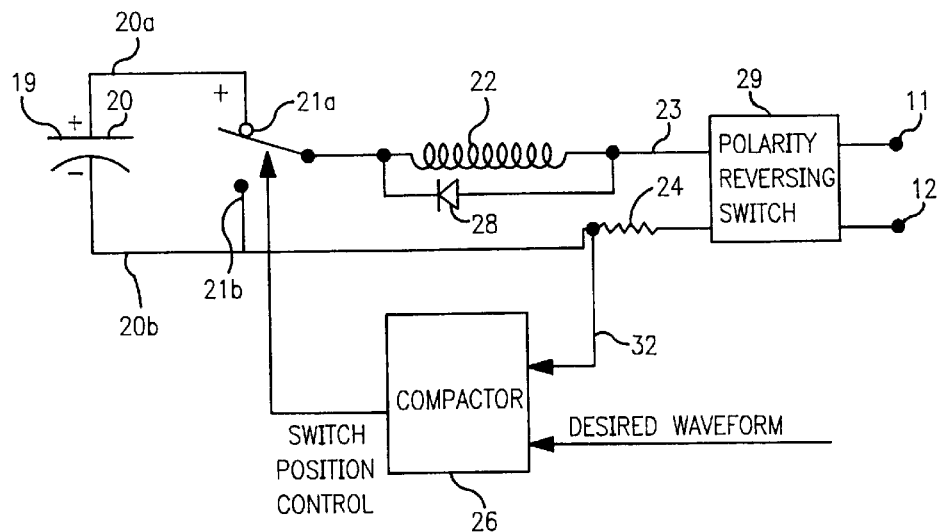
FIG. 2 is a schematic diagram of the defibrillator shown in FIG. 1.
Figure 3:
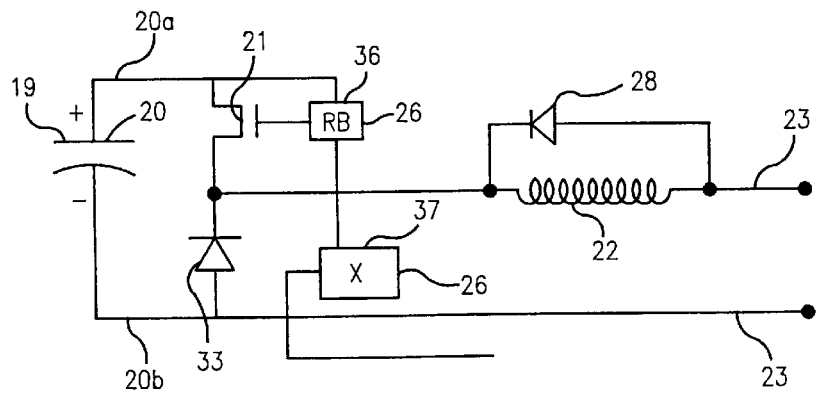
FIG. 3 is a schematic diagram of the defibrillator shown in FIG. 1.
Figure 4:
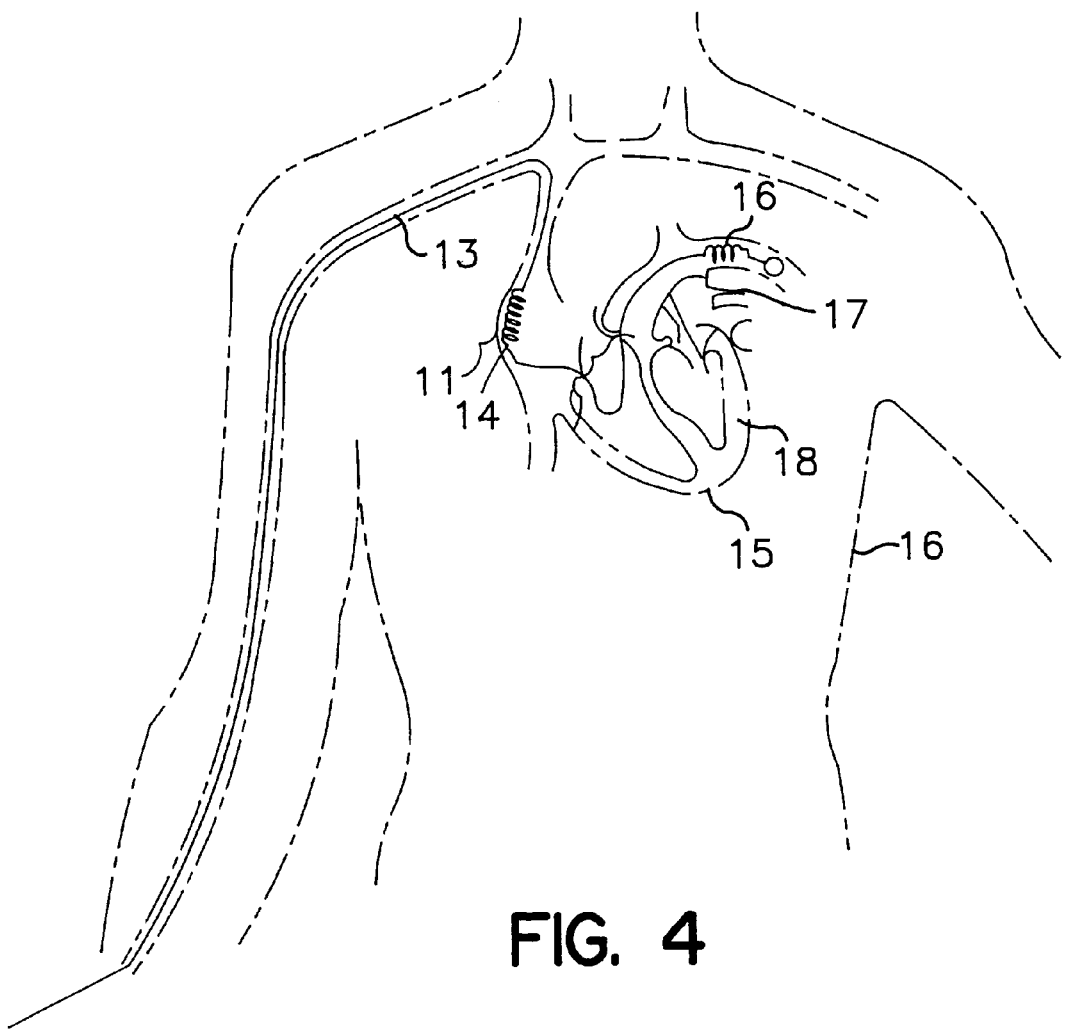
FIG. 4 is a view, partially in phantom, showing details of a defibrillating catheter in the heart of a patient.

Referring now to FIGS. 1, 2 and 3 of which FIG. 2 is a more detailed view of the circuit in FIG. 1 and FIG. 3 is a detailed view of a portion of the circuit of FIGS. 1 and 2, a high voltage supply 19 which includes a 150 microfarad capacitor bank 20 receives voltage from a suitable source such as a step-up transformer or the like which need not be shown. The capacitive discharge current used for defibrillation is supplied over a pair of capacitor leads 20a and 20b to a switch 21. In this embodiment the switch be a field effect transistor. The switch 21 is coupled to a 5 millihenry inductor 22 for providing pulse shaping. The inductor 22 is coupled to an output for providing a defibrillation current pulse to the patient.

The output 23 has associated with it a sensor 24 which supplies an output feedback signal on a line 25 to a controller 26. The controller 26 then signals the switch 21 to open and close rapidly in order to provide a substantial uniform defibrillation current pulse. It may be appreciated that one of the terminals for the switch 21, terminal 21a, is coupled to the positive side of the capacitor bank 20 while the other terminal 21b is coupled to the negative or ground side of the high voltage supply or capacitor bank 20. The switch is rapidly between the positive and negative terminals under the control of the controller 26 to provide the uniform defibrillation current pulse.

A protection diode 28 is connected across the inductor 22. The sensor 24 may comprise a current sensing resistor connected in the current loop as shown in FIG. 2. The output may be connected to polarity reversing switch 29 which may be a double-pole double-throw switch for reversing the direction of the output current during a portion of a defibrillation current pulse to provide a biphasic defibrillation pulse. The controller 26 may include a comparator which receives a desired defibrillation pulse waveform on a line 31 and compares it to the sensed defibrillation pulse waveform on a line 32. In response, the controller 26 generates the switch position control signal depending upon whether the current being sensed at the sensor 24 is above or below limits related to the desired waveform. The actual switching arrangement may also include a normally reverse-biased diode 33 coupled between the node of the field effect transistor 21 and the inductor 22 and the negative capacitor lead 20b. The diode 28 will provide a current path for allowing defibrillation current to continue to flow through the inductor 22 when the FET 21 is cutoff, effectively connecting the inductor 22 to the negative terminal of the high voltage capacitor bank 20.

Referring now specifically to FIG. 3, the high voltage capacitor bank 20 has its output current flow controlled by the field effect or EGFET transistor 21, which functions as a fast high voltage switch device. The field effect transistor or switch 21 selectively couples the positive terminal of the high voltage capacitor 20 to the inductor 22 and when the transistor open circuits the inductor 22 is connected effectively in the circuit with the fast high voltage diode 33. Thus, the inductor 22 is toggled effectively between the positive supply voltage 20a on the capacitor bank 20 and the negative supply voltage side 20b of the capacitor bank 20.

The switch toggling is controlled by the controller 26. It includes a level shifting transmitter 37 coupled to receive a signal from another portion of the controller which compares the sensed current pulse to the desired waveform. The level shifting transmitter 37 in turn signals a level shifting receiver 36 which is coupled to the gate of the field effect transistor 21 causing it to switch. The level shifting transmitter 37 and the level shifting receiver 36 provide buffering in order to drive the high voltage field effect transistor. Among other portions of the comparator 26 the transmitter 37 receives a signal which is level shifted and then sent to the receiver 36. The link between the transmitter 37 and the receiver 37 may be electrical, optical or inductive although inductive or optical transmission links would be most desirable.

When the sensed waveform from the line 32 exceeds the desired waveform by about a 10% factor the signal will be supplied to the transmitter 37 to command the receiver 36 to switch the transistor 21 off. This will cause the diode 33 to be forward biased and in the current loop with the inductor 22 effectively connecting the inductor to the negative terminal potential less the diode forward drop. During the switching transition the protective diode 28 will provide a current flow path for current in the inductor 22.

Figure 5A:
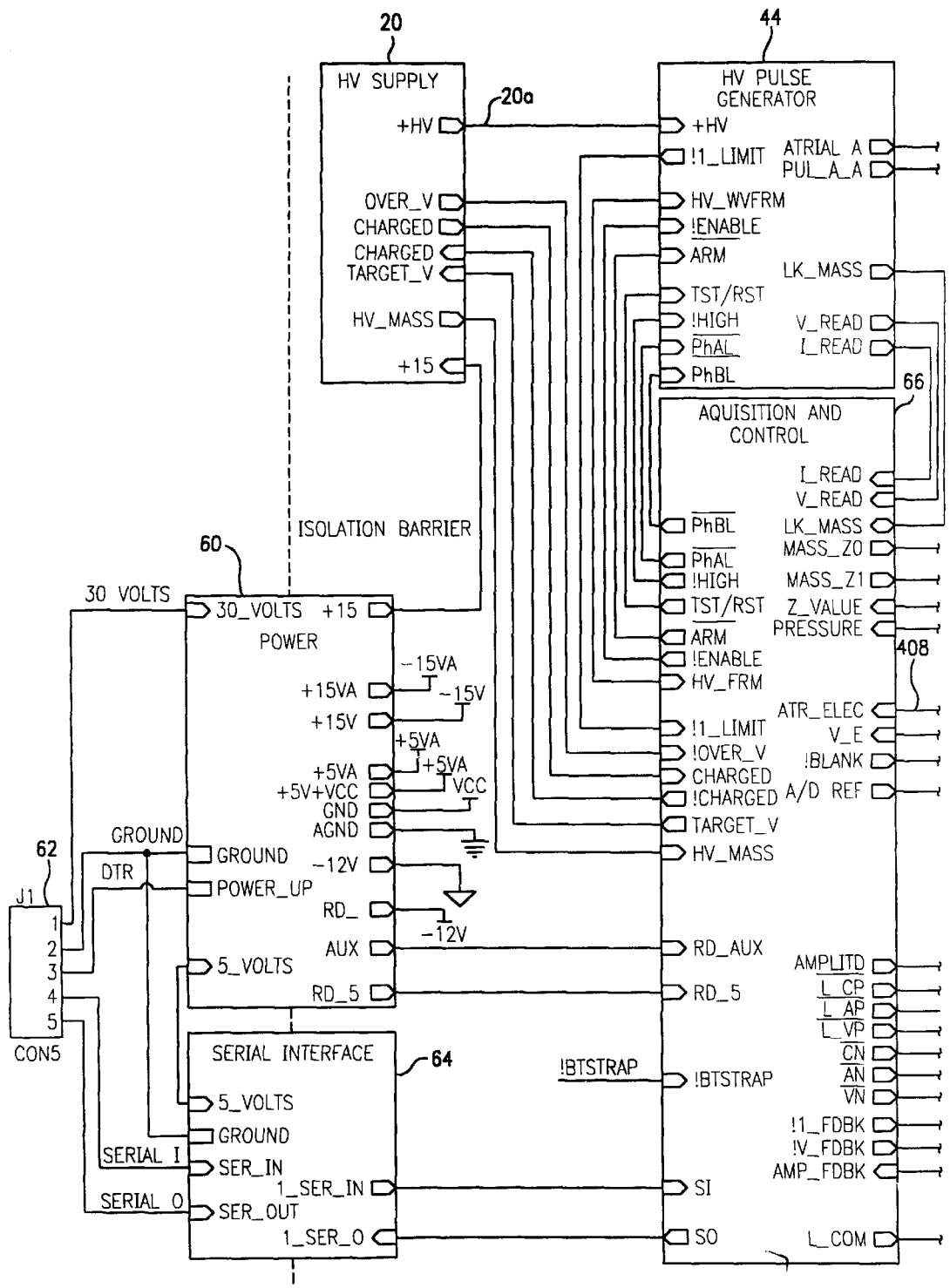
FIG. 5 is a block diagram of the defibrillator shown in FIG. 1.
Figure 5B:
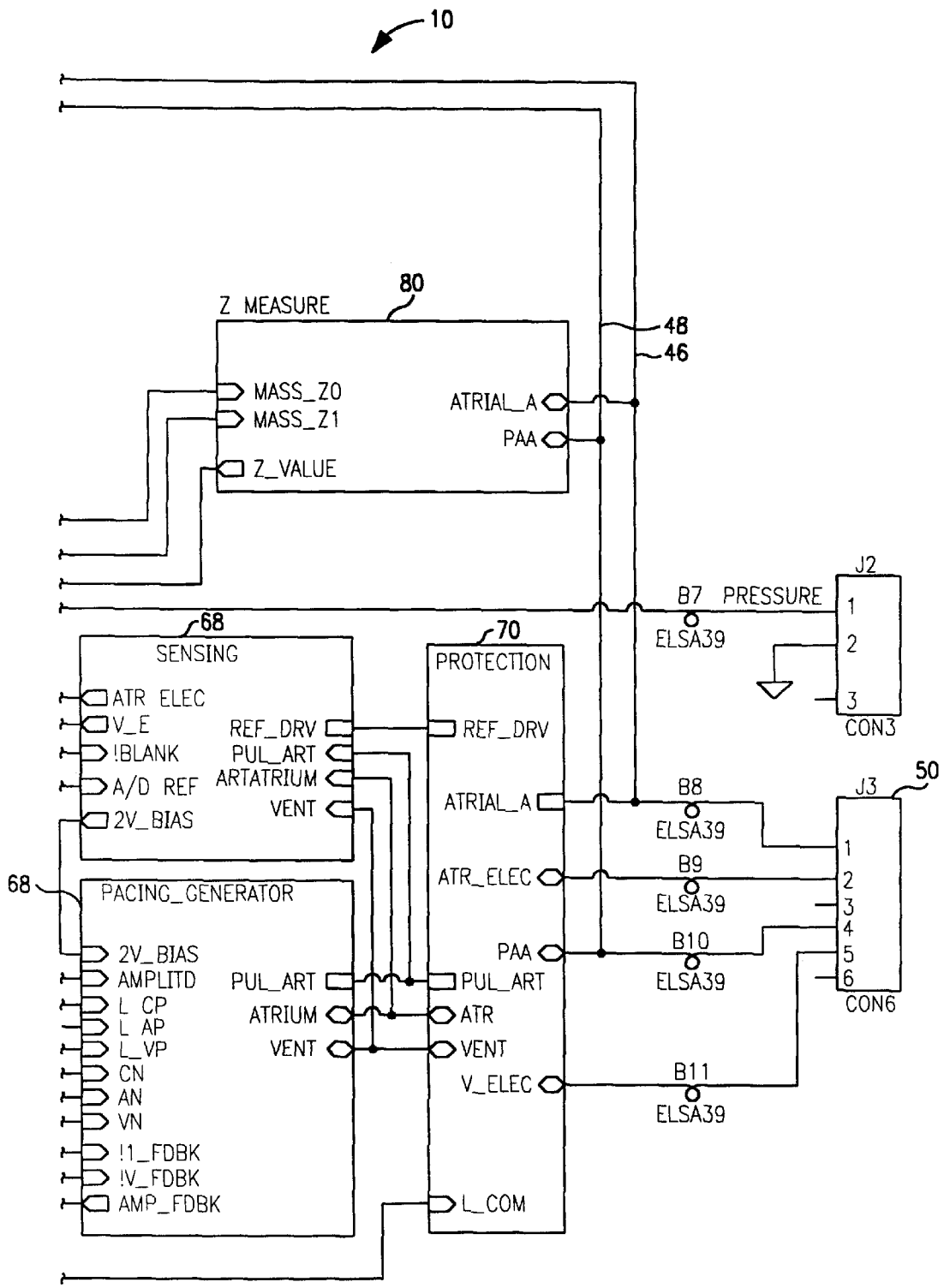

Referring now to FIG. 5, the high voltage supply 19, including the 150 microfarad high voltage capacitor bank 20, is connected by a high voltage supply line 42 to a high voltage pulse generator 44. The high voltage pulse generator 44 delivers atrial defibrillating current in the form of a current pulse via a pair of defibrillating current lines 46 and 48 to a catheter connector 50. The catheter connector 50 is releasably and electrically connected to the Swan-Ganz catheter 13 to receive the defibrillating current pulses from the high voltage pulse generator 44 and carry them to the catheter electrodes 11 and 12.

The high voltage supply 40 is primarily energized from a low voltage power supply 60 coupled to receive power from a connector 62. A serial interface 64 communicates data to an acquisition and control circuit 66.

The data acquisition and control circuit 66 also is coupled to a sensing circuit 68 to receive information via a high voltage protection circuit 70 from the Swan-Ganz catheter 13 connected to the connector 50. The data acquisition and control circuitry 66 controls generation of the defibrillating pulse by the high voltage pulse generator 44. A Z-measure circuit 80 may optionally be included for measuring the impedance of the patient circuit comprising the patient and catheter. The patient circuit impedance measurement may be used by the data acquisition and control circuit to adjust the defibrillation pulse parameters.

Figure 6A:
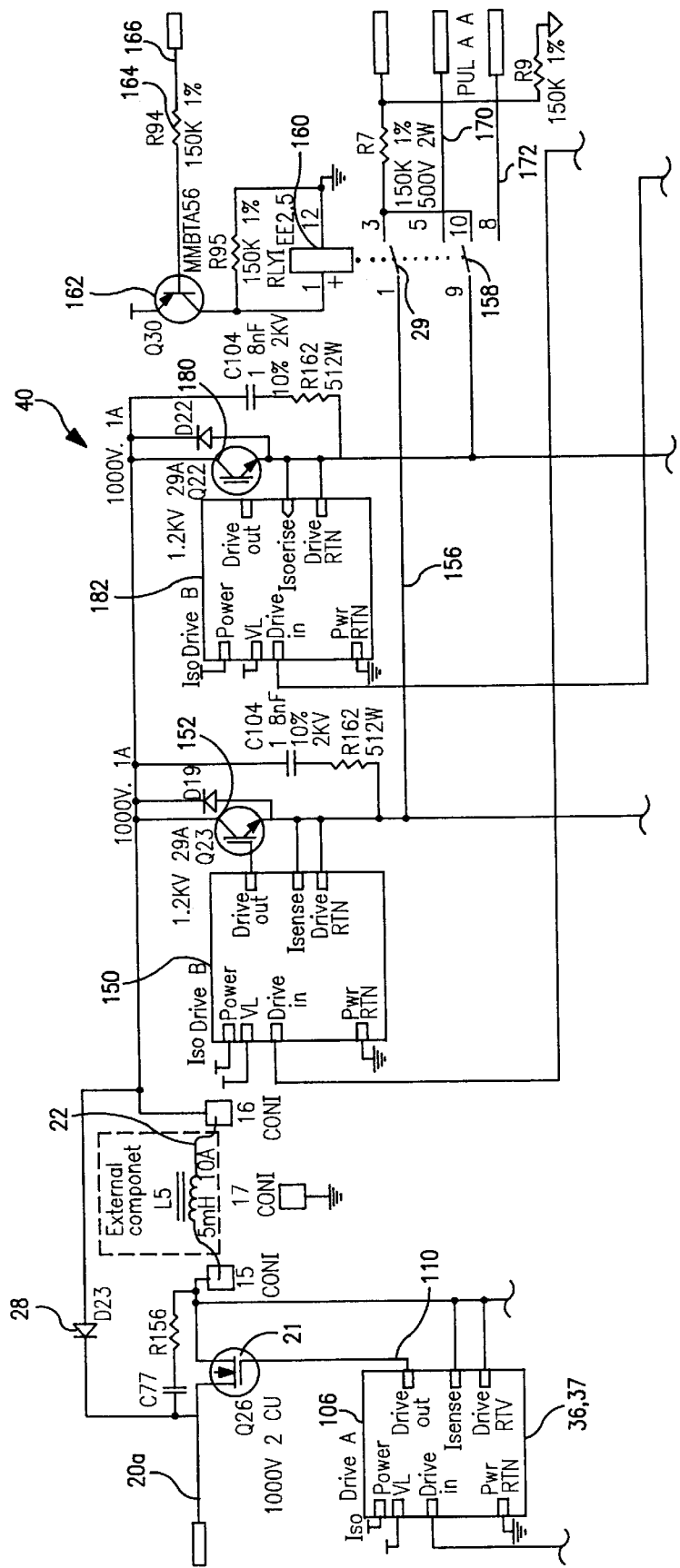
FIG. 6 is a schematic diagram of a high voltage pulse generator of the defibrillator shown in FIG. 5.
Figure 6B:
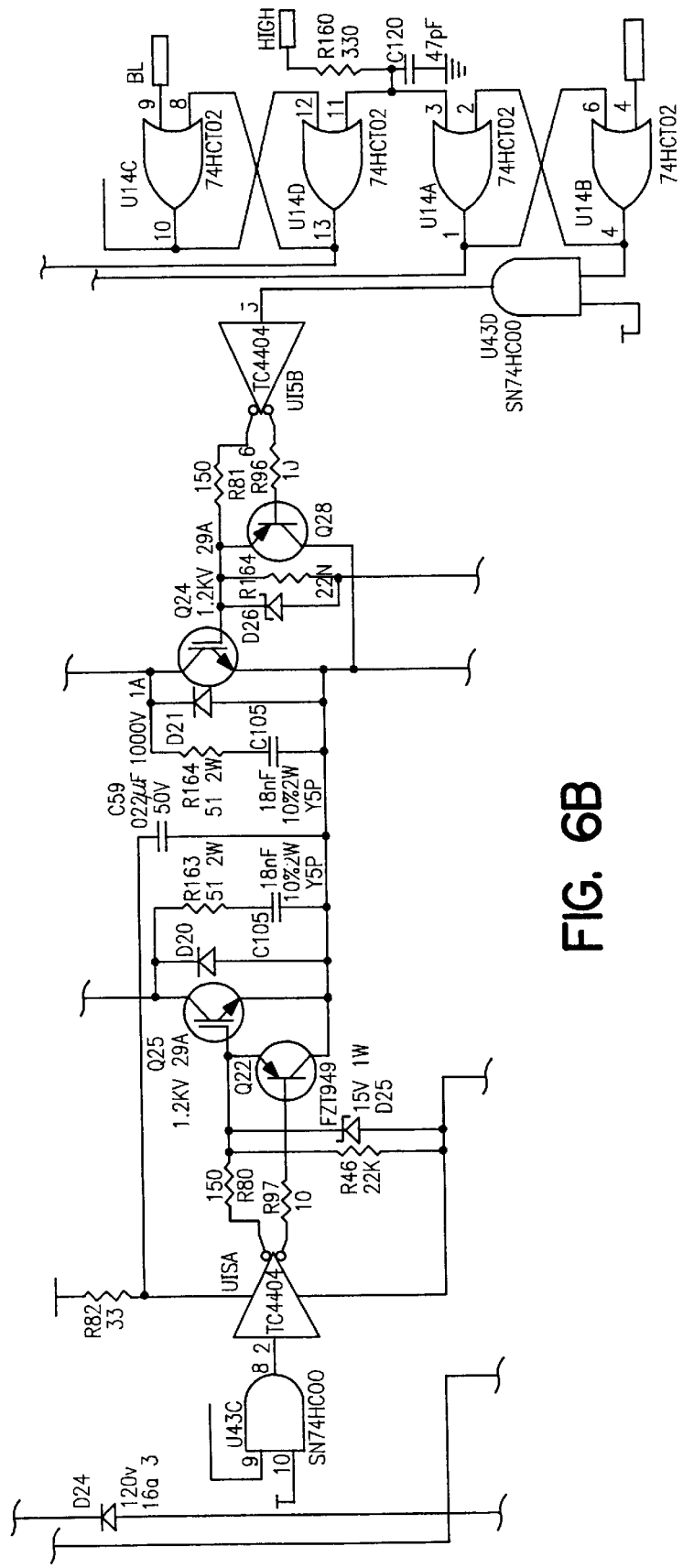
Figure 6C:
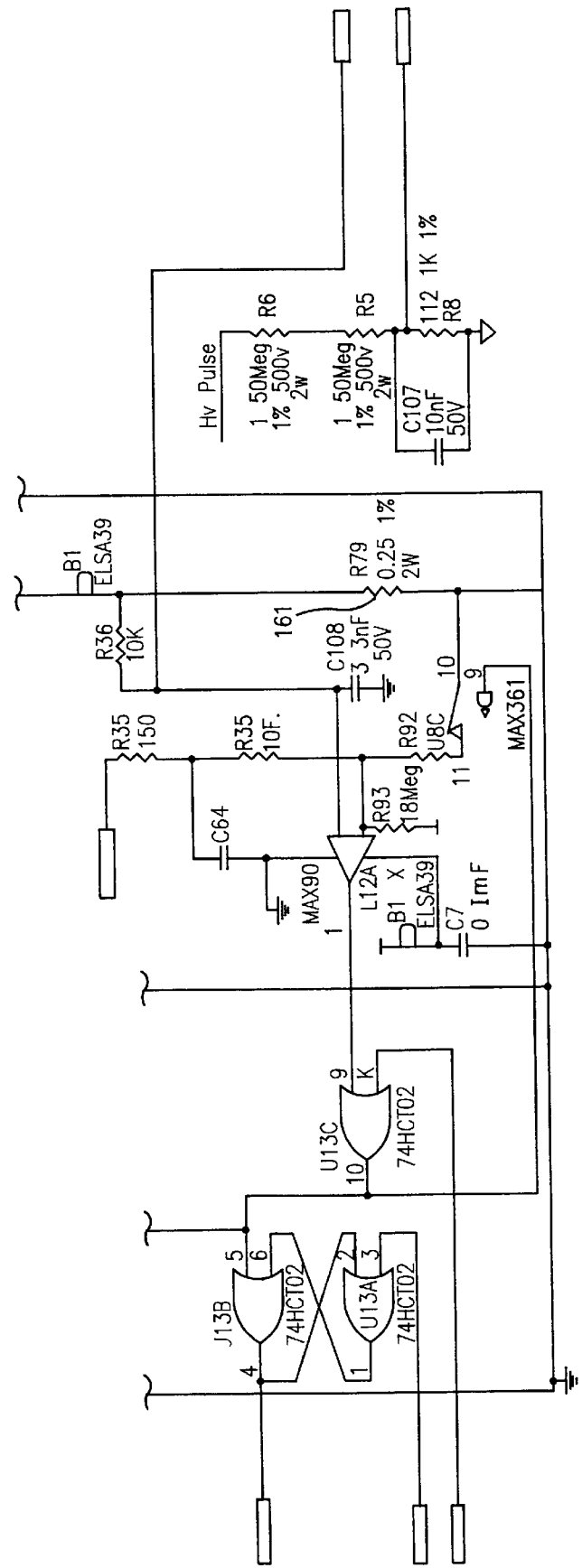
Figure 7A:
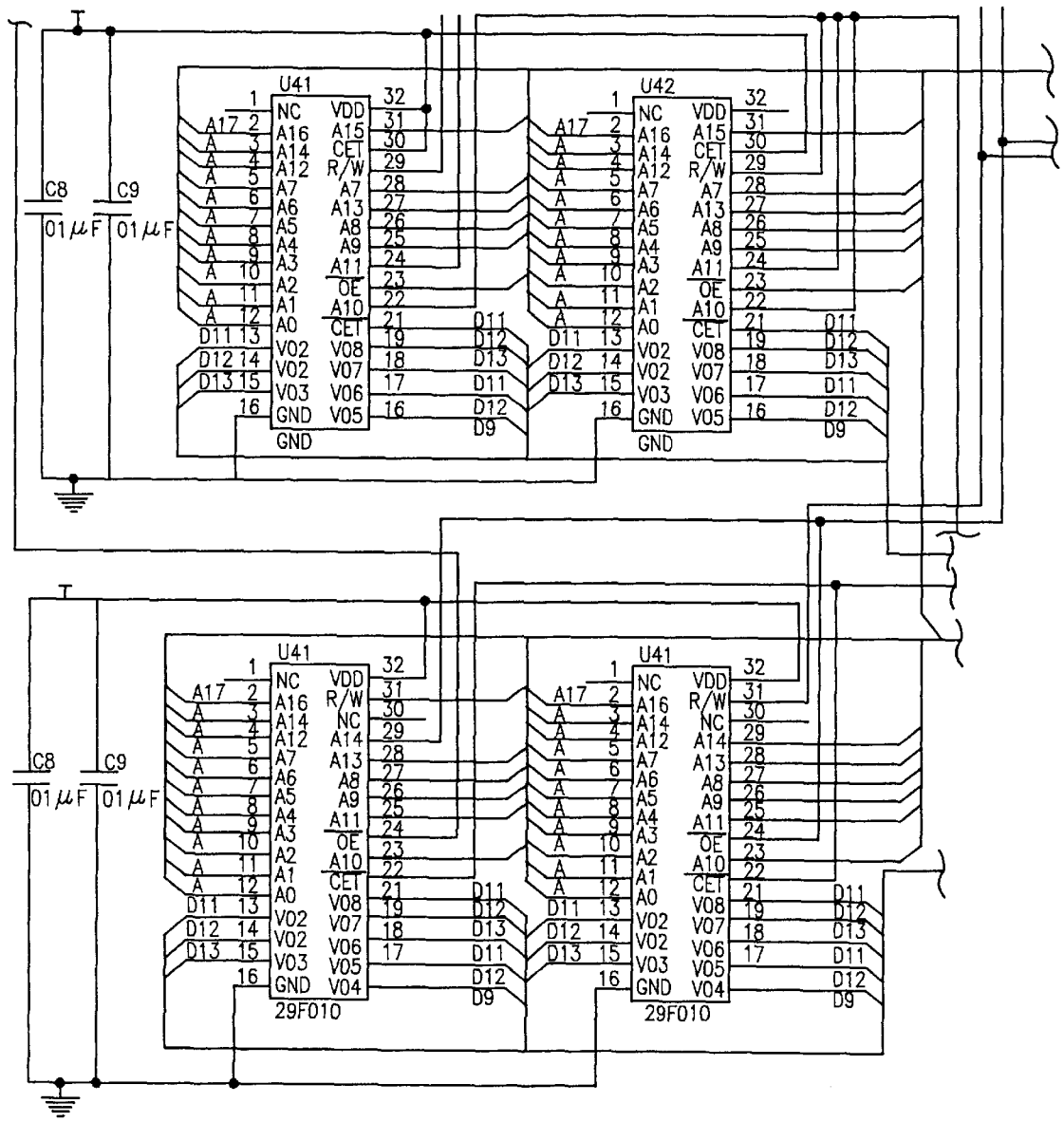
FIG. 7 is a schematic diagram of a data acquisition and control current of the defibrillator shown in FIG. 5.
Figure 7B:
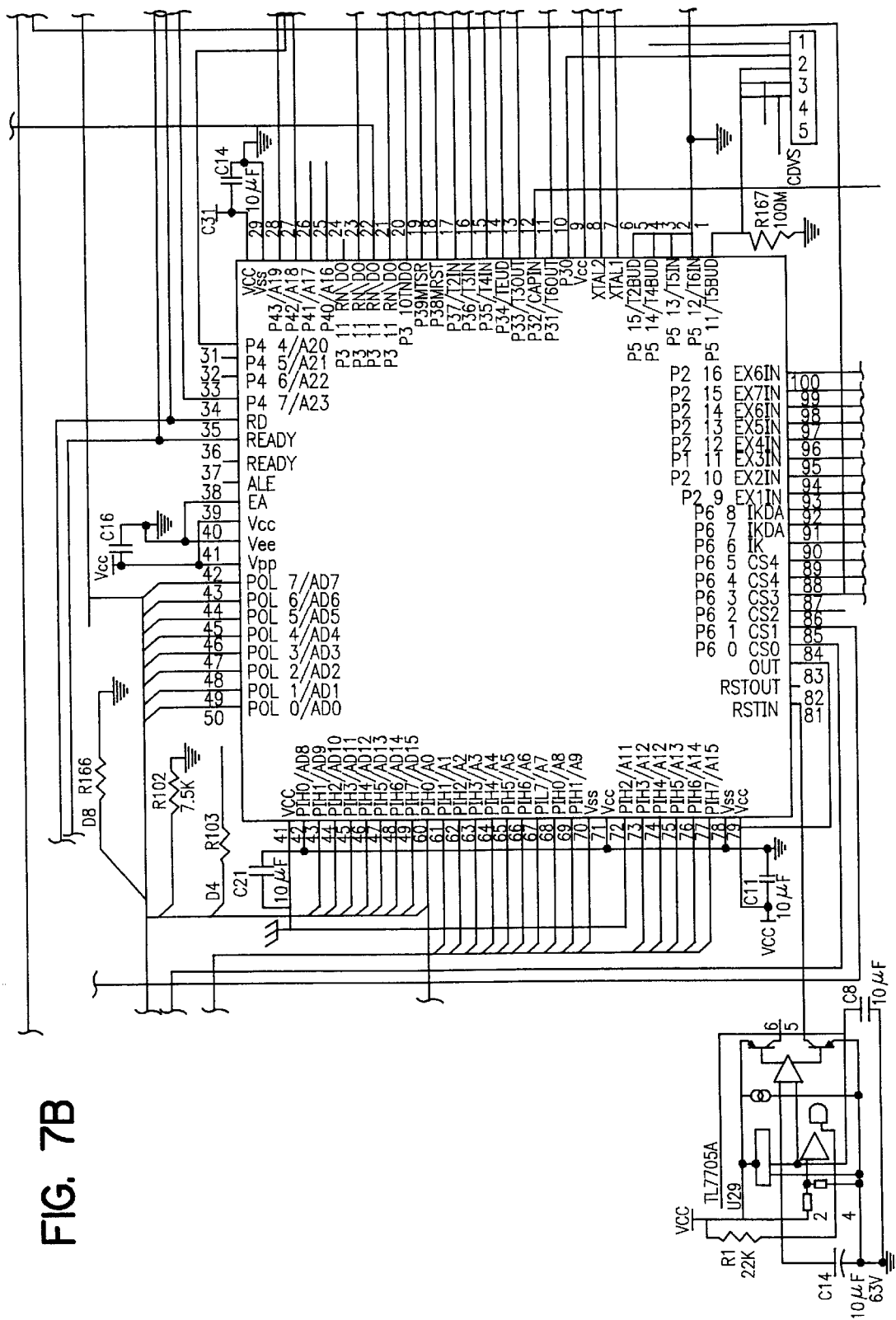
Figure 7C:
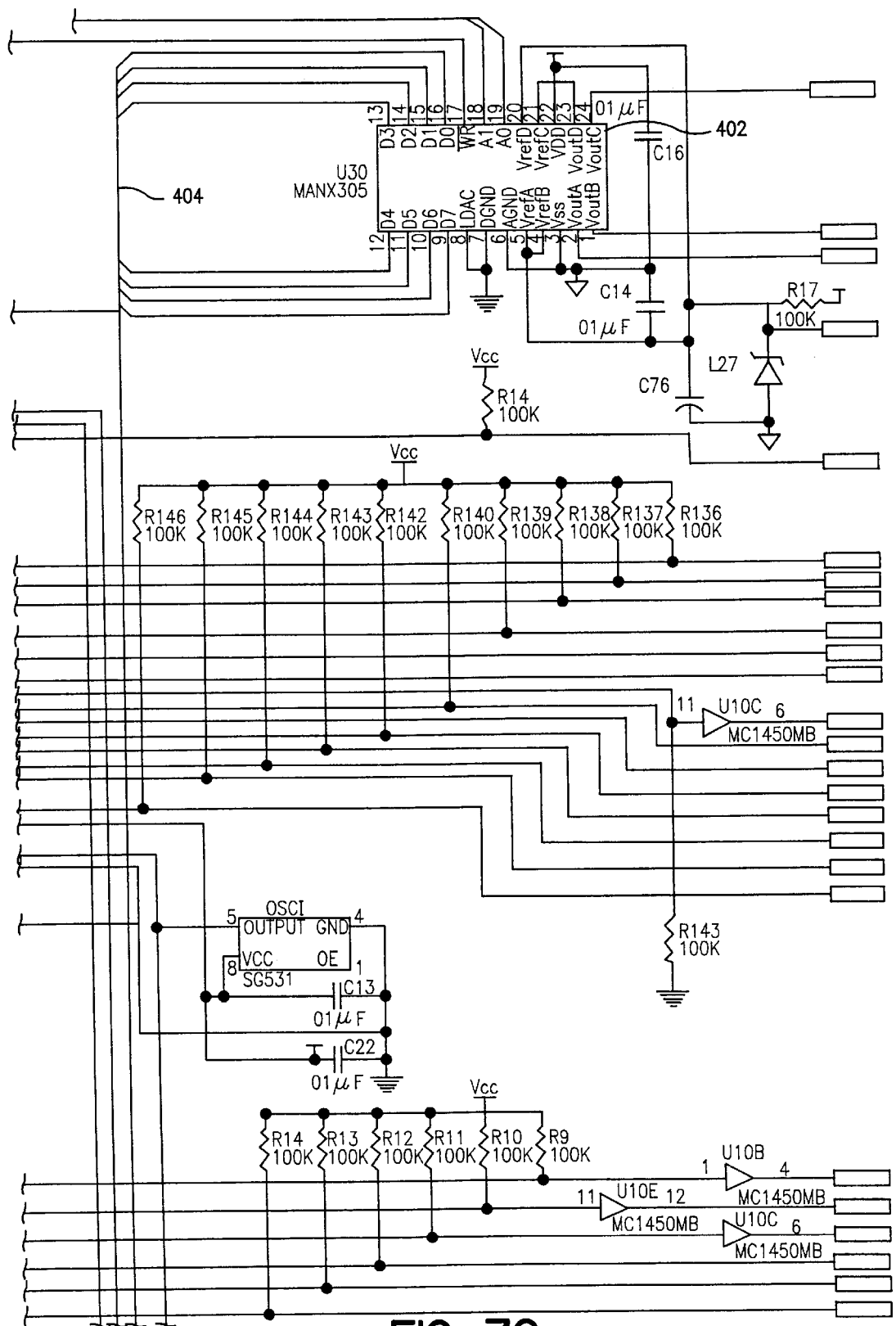
Figure 7D:
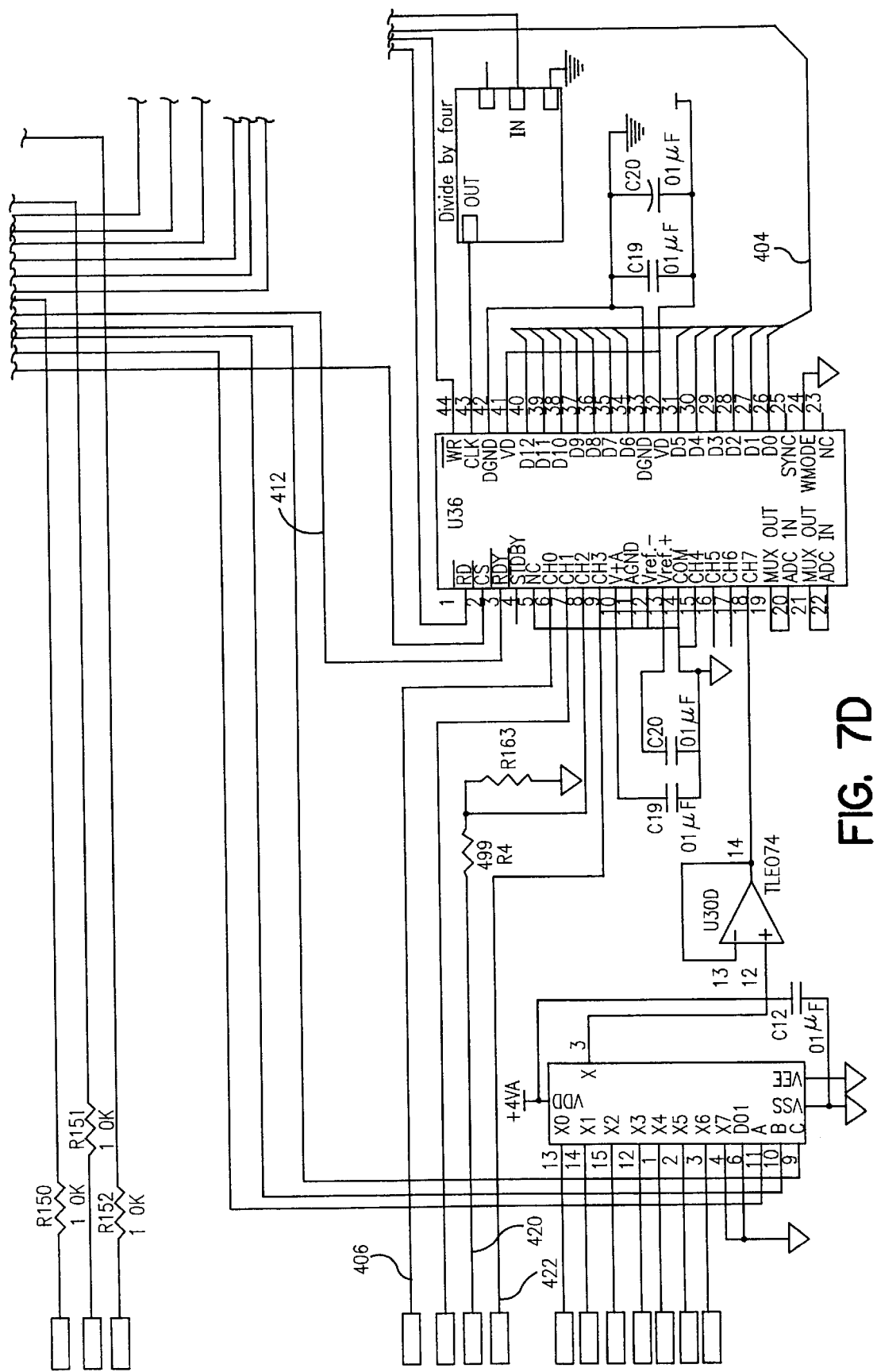

As is shown in FIG. 6, the high voltage pulse generator 44 has a high voltage input 90 from the high voltage line 92. The high voltage input is coupled via the capacitor switching transistor 21 to the inductor 22. The capacitor switching transistor 21 is controlled at its gate 110 by a control signal provided from an isolated driver 106.

Figure 8:
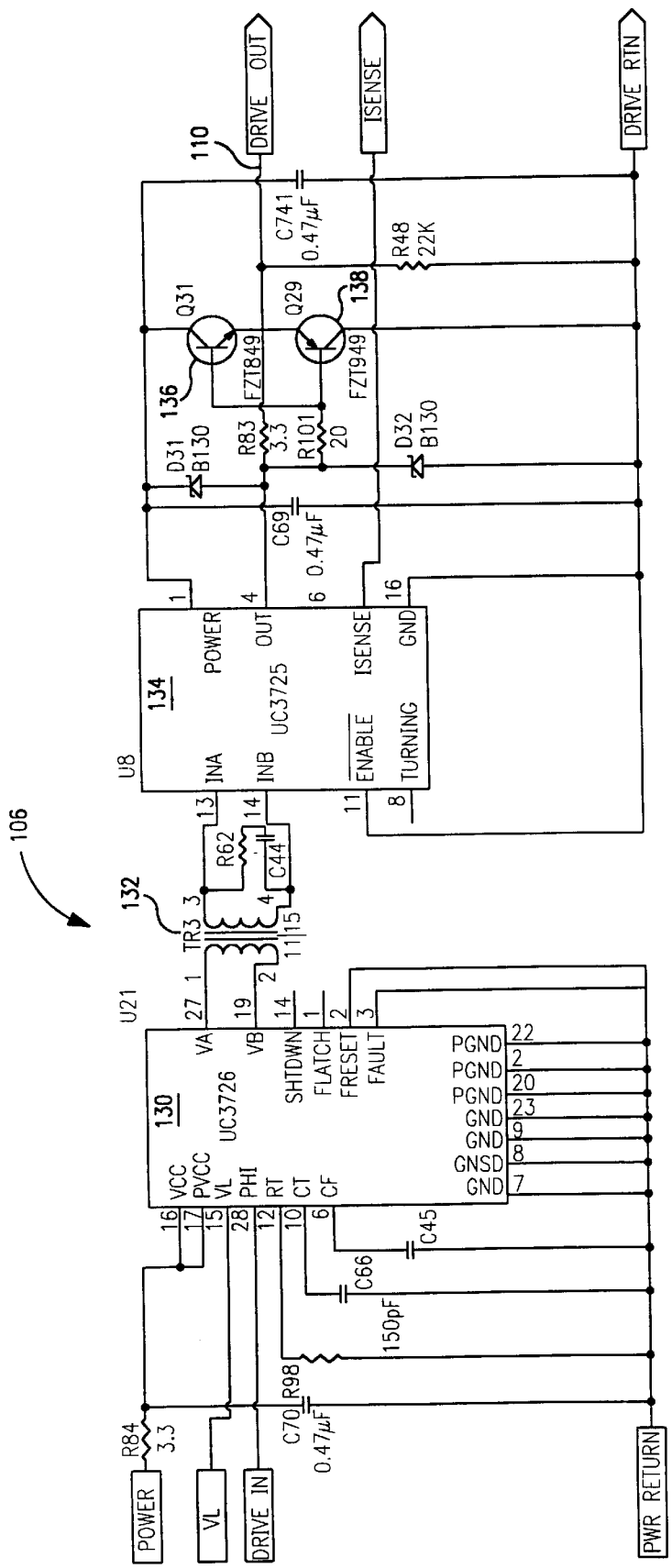
FIG. 8 is a schematic diagram of a first isolated gate driver for the defibrillator shown in FIG. 5.

As may best be seen in FIG. 8, the isolated driver 106 controls the capacitor switching transistor 21. The isolated driver 106 has a Unitrode 3726 isolated transmitter integrated circuit 130 which supplies electrical energy through an isolation transformer 132 to a Unitrode UC3725 isolated driver integrated circuit 134. The isolated driver 134 controls the switching of a pair of bipolar transistors 136 and 138 to bias a DRIVEOUT line 109 connected to the gate 110. The control on the DRIVEOUT line 110 is used to control the capacitor current and enables current flow in the inductor 22.

A second isolated drive 150 is connected to a transistor 152 to control delivery of defibrillating current to a line 156. The line 156 is coupled to a double-pole double-throw switch 158, which is a portion of the polarity reversing switch 29, comprising a portion of a relay 160. The state of the relay 160 is controlled by a transistor 162 biased through a resistor 164 from an arming line 166 driven by a microcontroller in the acquisition and control circuit 66. The output of the double-pole double-throw switch 158 is via the lines 170 and 172 which are respectively connected to the atrial electrode 14 and the pulmonary artery electrode 16. Another transistor 180 is controlled through an isolated drive 182.

Figure 9:
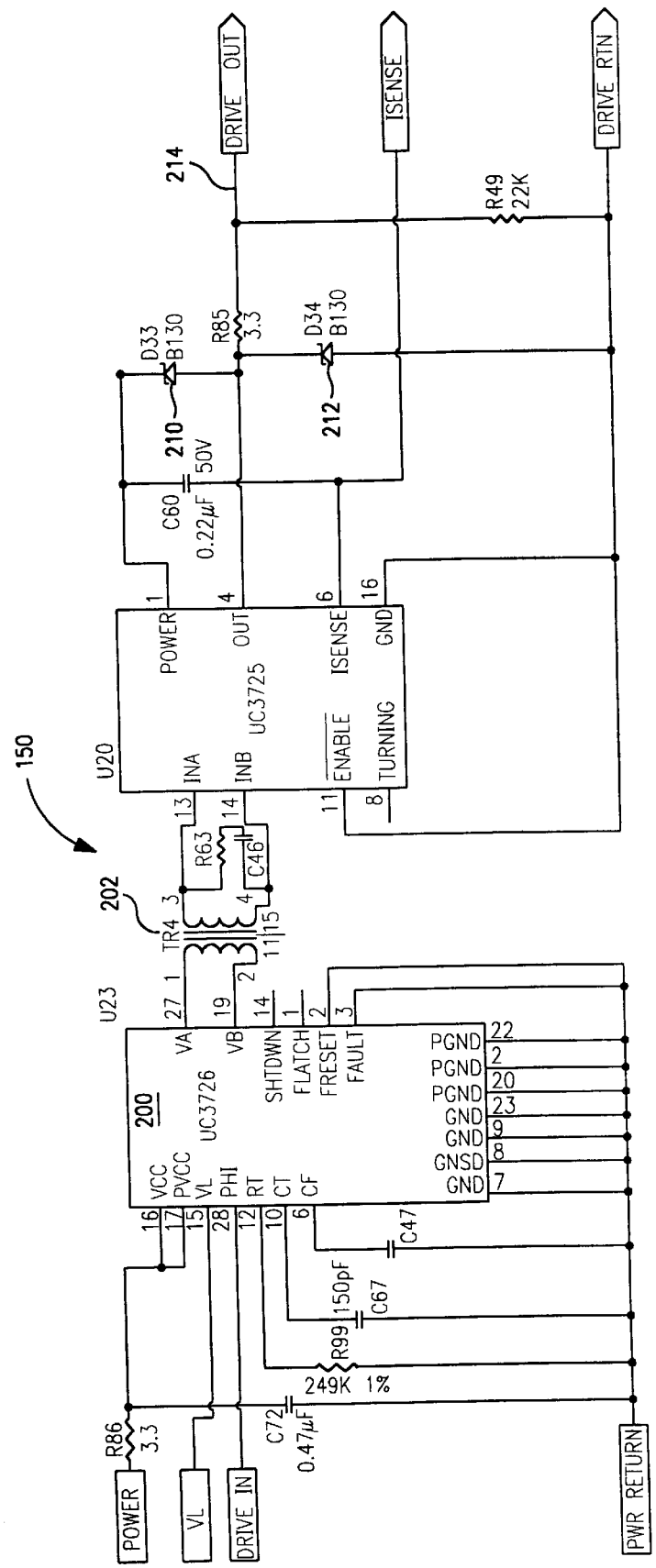
FIG. 9 is a schematic diagram of a second isolated gate driver of the defibrillator shown in FIG. 5.

The isolated gate drive 150 as may best be seen in FIG. 9 includes a Unitrode UC3726 isolated drive transmitter 200. The isolated drive transmitter is connected to receive power and also to supply an output through an isolation transformer 202. The isolation transformer 202 isolates the high voltage line from the high voltage drive from other portions of the circuit. The isolation transformer sends control signals to a Unitrode UC3725 integrated circuit which supplies full-wave rectified DC power to a pair of Zener diodes 210 and 212. The zener diodes limit voltage swings from the DRIVEOUT pin 214 which is coupled to the transistor 152 to control switching of high voltage atrial defibrillation current into the line 156.

Figure 10:
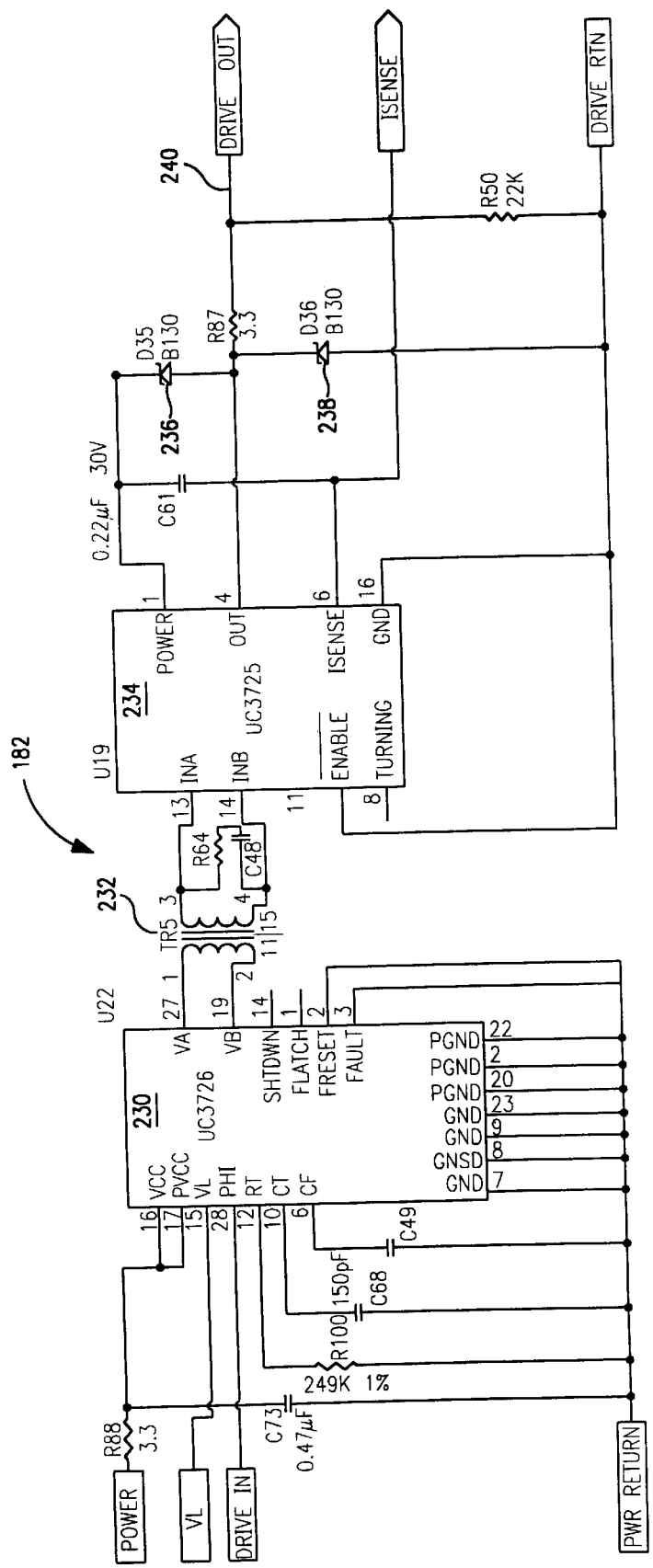
FIG. 10 is a schematic diagram of a third isolated gate driver of the defibrillator shown in FIG. 5.

Likewise, the isolated gate drive 182 as may best be seen in FIG. 10, includes a Unitrode UC3726 isolated drive transmitter 230 coupled to an isolation transformer 232 for isolating the high pulse from other portions of the circuit, and to the UC3725 circuit 234 to an identical Zener pair 236 and 238 for providing base drive out on a drive 240 to the transistor 180.

Referring now to the data acquisition and control circuit 66, the circuit includes a microcontroller 400 coupled to a Maxim 505 quad 8-bit digital to analog converter 402 to receive digital signals on a bus 404 and produce analog outputs for supply to other portions of the circuit.

The microcontroller 400 is coupled to an analog to digital converter 412 for receiving a variety of analog signals, for instance, from the atrial electrode 406, the signal related to blood pressure on an electrode 420 and a Z-value on an electrode 422. The signals are converted to digital signals and sent over the bus 404 to the microcontroller 400.

The current control feature embodied in high voltage pulse generator 44 including the inductor 22, the diode 103, the resistor 161 and the current waveform control means 26 embodying the present invention operates with the capacitor 20 rated greater than 700 volts to an initial value of voltage $V_s$. The double-pole, double-throw relay switch 158 connecting the pair of heart electrodes 11 and 12 in the catheter 14 through the high voltage capacitor 20 during the defibrillating pulse generation and during changes in polarity to deliver a biphasic (or multiphasic) pulse, the impedance measuring means 80 is connected across the heart electrodes 11 and 12 in the catheter 13 to measure resistance and uses lower amplitude, substimulation voltage to obtain such impedance, and the microcontroller 400 provides a control means capable of real time control during pulse generation.

The inductor 22 operates as a nearly perfect inductor when energized with defibrillation current of up to 10 amperes. The switch 21 can switch the inductive current I(t) (which is also the controlled-current delivered through the heart) to either the high-voltage source capacitor bank 20 in the high voltage supply 40 with voltage, $V_s$, at the upper position or to ground, at the down position. The position of the switch 21 is controlled by the current waveform control means 26. The diode 28 prevents the output voltage $V_0$ from exceeding the capacitor voltage $V_s$ during interruptions in I(t) through the heart, that is, during polarity reversal or at the end of a pulse. The current sensing resistor 24 with a calibrated value of 0.25 ohm is in series with the current path of the inductive current immediately above the ground return.

Figure 13:
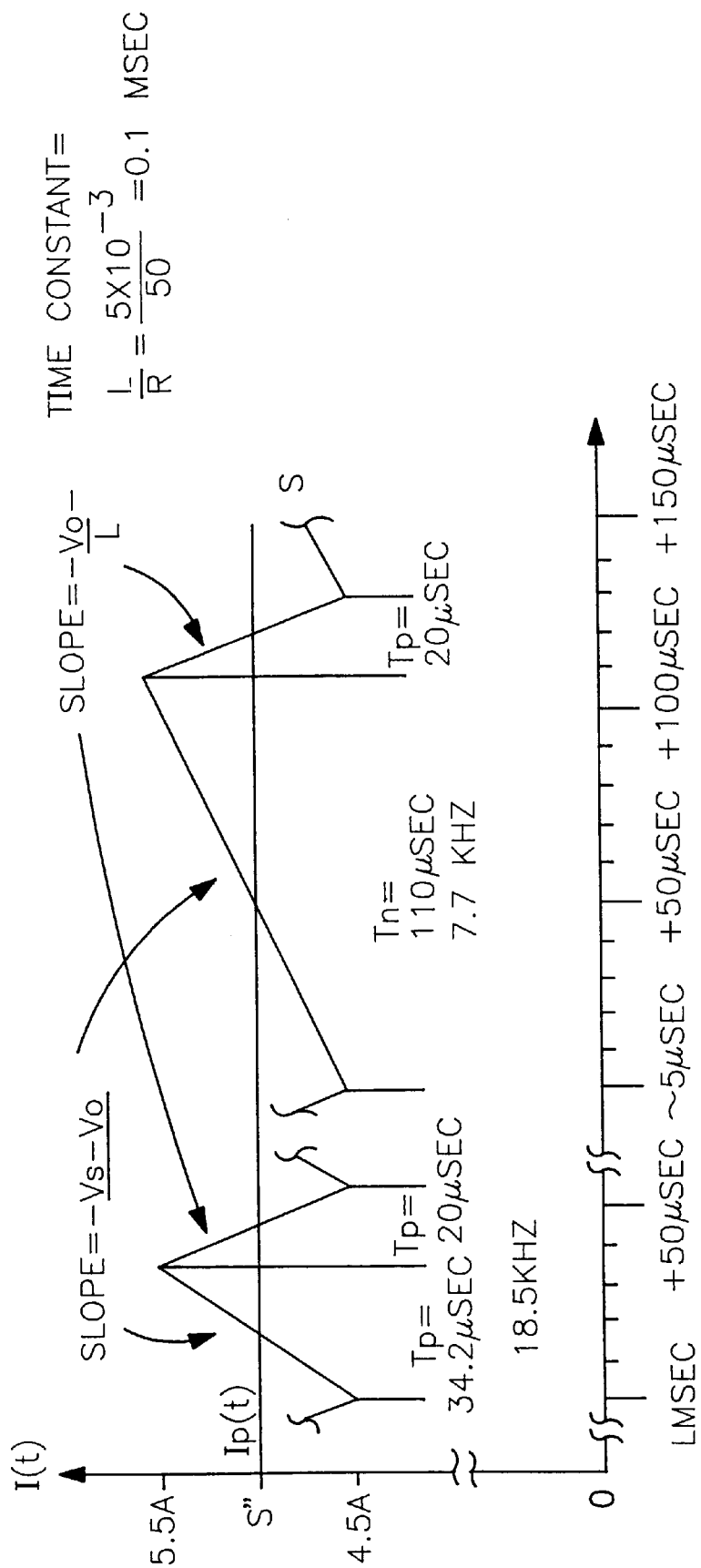
FIG. 13 is a graph of current with respect to time showing details of the sawtooth width at two different switching frequencies.

In operation controlled current atrial defibrillation is achieved by the operation of the microcontroller 400 and associated switching circuitry. The microcontroller 400 is programmed to deliver the constant current biphasic waveform shown in FIG. 13, $I_p(t)$ The waveform consists of a linear ramp up to 5 amperes over a duration of 1 millisecond. A sustaining level of 5 amperes for 4 milliseconds follows the ramp. Polarity is then reversed and a 3 ampere current is sustained at reverse polarity for 2 milliseconds.

In order to provide the controlled current the microcontroller 400 first senses the low voltage resistance value assumed to be about 50 ohms. The microcontroller 400 then calculates the necessary initial voltage needed across the capacitor. It then causes the high voltage supply 40 to charge the capacitor bank 20 to the selected voltage, for instance, 450 volts. The microcontroller 400 then causes the switch 160 to close in the positive position. This allows the programmed waveform to be sent in real time to the current waveform control means either in a digital or an analog format.

The control waveform control means 26 measures the voltage across the low resistance resistor 24 through a high impedance. It continuously compares the resulting measured current to a pair of ideal current waveforms. The pair would typically be the programmed waveform increased by 10%. $I_p(t)$ and the programmed waveform decreased by 10% factor $I_{p-}(t)$. The current waveform control means controls the switch. When the actual measured current is greater than the positive current the switch is connected to ground. If the actual measured current is less than or equal to the lower 10% value the switch 21 is connected to the defibrillating capacitor 20.

At the beginning of the defibrillating pulse the switch 21 will be in the upper position. Current will begin to flow from the capacitor 20 through the inductor 22 and the patient's heart 15, preferably the atrium 17. Within a small fraction of a millisecond the defibrillating current will be equal to $I_{p+}(t)$. The control means 26 will cause the switch 21 to be connected to the negative terminal 20b. The defibrillating current will then decrease slowly at first because $V_0$ is equal to 20. Eventually I(t) will become equal to $I_{p-}(t)$ causing the switch to reconnect to the capacitor bank 20 and allowing the current to flow through the inductor 22 again. The resulting delivered current waveform is the programmed waveform plus a five sawtooth waveform ±10%.

Figure 11:
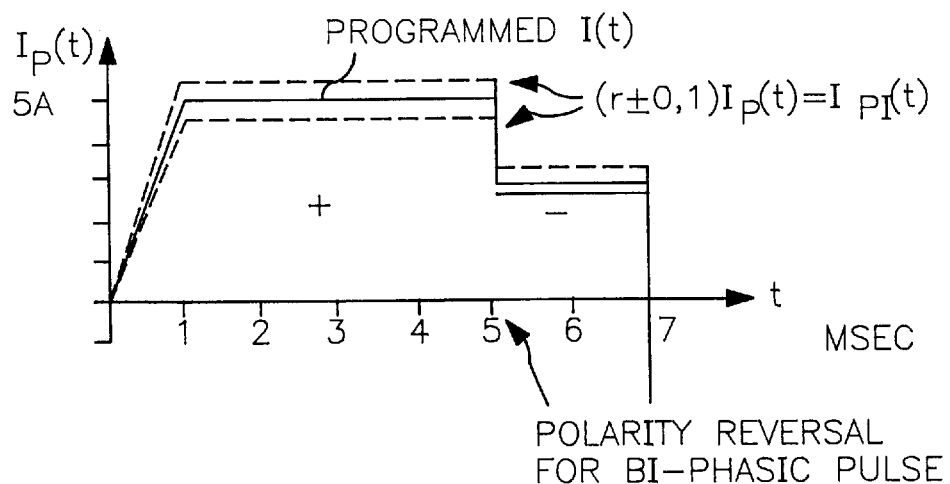
FIG. 11 is a graph of current versus time showing details of the biphasic nature of the defibrillating current produced by the defibrillator shown in FIG. 5.
Figure 12:
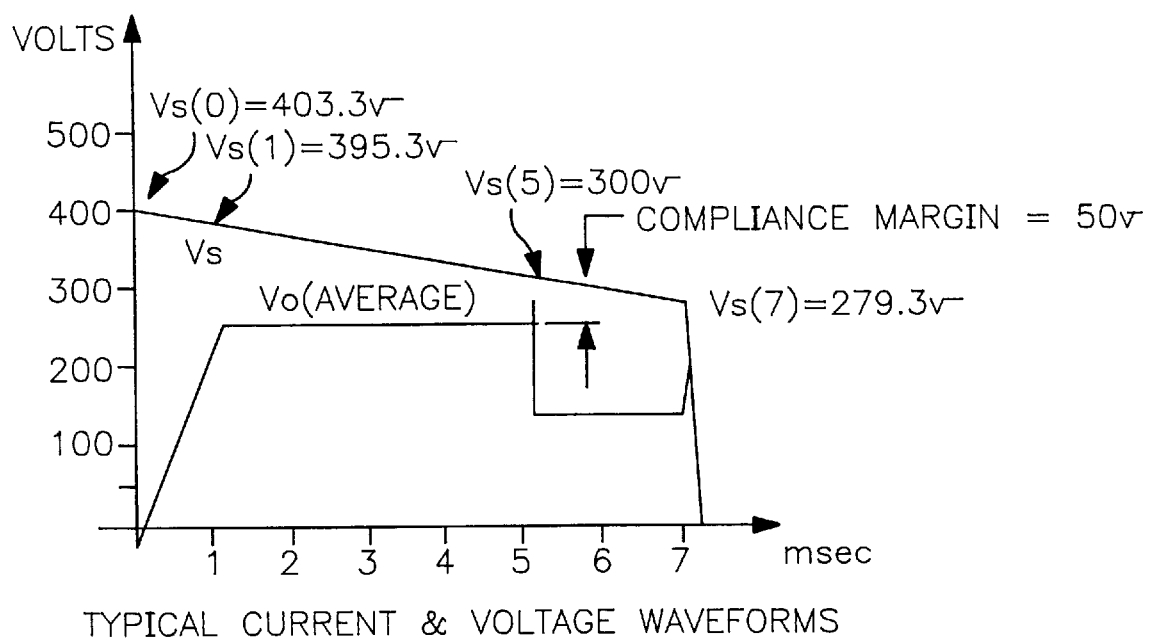
FIG. 12 is a graph of voltage with respect to time across the heart of a patient.

As may best be seen in FIG. 11, the output voltage $V_0$ and the decreasing capacitor voltage $V_s$ during the pulse shown on a millisecond time scale corresponding to the fine sawtooth $V_s$ would appear to be a staircase. Constant voltage portions correspond to the intervals when the switch $S_1$ is connected to ground. The steps in the output voltage waveform are connected by ramps whose slopes are given by $I_p(t)/C$.

The millisecond time scale voltage, $V_s$ on the capacitor is given by the equations following as a function of time during the waveform. The equations are derived from conservation of energy considerations and include in the energy budget the energy stored in the inductor 102, about $\frac{1}{16}$ joule, which is relatively minor. Because of the conservation of energy considerations more of the energy from the defibrillating capacitor bank 20 is delivered to the heart 15. The small amount of energy transferred to the inductor 22 is either delivered to the heart 22 or dissipated in the diode 28, depending upon the switching sequence of the switches 21 and 158 at the time when the polarity is reversed and at the end of the pulse.

In general, the capacitor voltage is given by $$V(t) = \sqrt{\frac{2}{c}\Delta E(t) - V_0^2(0)}.$$

In the above expression, $\Delta E(t)$ represents the energy transferred from the capacitor as a function of time during the course of the pulse application.

The microcontroller 400 functioning in accordance with the aforementioned equations as models determines the initial voltage to which the capacitor bank 20 must be charged in order to deliver the desired current waveform. In order to do so, it first determines the point in time during the waveform when $V_s-V_0$ is at a minimum. In the aforementioned example the minimum is at T=5 milliseconds at the end of the 5 ampere constant current positive pulse. The microcontroller 400 then calculates $V_0(t)$=5 amperes×50 ohms to yield 250 volts for the minimum emf to drive the 5 ampere current. It then adds a programmed compliance margin voltage, in the present instance of 50, volts to select $V_s$ at S=300 volts. The microcontroller 400 then calculates the amount of energy to be removed from the capacitor during the first 5 milliseconds of operation, which is equal to $\Delta E(5)$. Neglecting the energy accumulated in the inductor 22, The initial voltage can be calculated from $$\Delta E(t) = R \int_0^t I^2(\tau) d\tau.$$

$$Vs(0) = \sqrt{V_s^2(5) + \frac{2}{c}\Delta E(5)}$$

During the first millisecond 0.416 joules will be delivered to the heart 15 and 0.0625 joules will be stored in the inductor 22. Therefore, the transfer of energy $\Delta E$ from the capacitor bank 20 during the first millisecond is 0.48 joules.

During each millisecond of the 5 ampere constant current portions 1.25 joules of electrical energy are delivered to the heart 15. Therefore, total energy transferred from the capacitor bank 20 during the 5 milliseconds is 5.48 joules.

The initial voltage required across the capacitor bank 20 is therefore $V_s(0)$=403.8 volts. As may be seen in FIG. 6, the detailed waveform of $I_t$ at t=1 millisecond and t=5 milliseconds, including the fine sawtooth since the 100 millisecond time constant divided by L/R is longer than the duration of one of the resulting sawteeth.

The sawteeth are approximately linear having positive slopes given by the quantity $(V_s-V_0)/L$. The negative slopes are given by $-V_0/K$. It can be seen that the switching frequency required to maintain the switch 21 within the 10 percent current control limits decreased from 18.5 kHz at the beginning of the 5 ampere constant current portion of the waveform 7.7 kHz at the end of the waveform as fewer current corrections were needed as the capacitor voltage decayed. The critical compliance point at 5 milliseconds corresponds to the lowest switching frequency during the entire waveform.

Although in some embodiments it may be possible to use sensing feedback to the polarity reversing switch 158 to regulate its closure to achieve the current control waveform this approach is undesirable. It would dissipate energy across the resistance of the switch 158 because current regulation would be achieved at the cost of partially closing the switch 158. Dropping the voltage drop across the switch 158 would create a controlled current source.

In the present example a total of 6.3 joules of electrical energy is delivered to the heart 15 during one biphasic defibrillation pulse. The capacitor bank 20 would need to be charged to 450 volts and the capacitor voltage would decrease to 250 volts during application of the pulse current to the heart 15. This corresponds to 10.1 joules of electrical energy being removed from the capacitor bank 20. The 3.8 joule energy difference is absorbed by the switch 158 during the 7 millisecond duration. This gives an average power input of about 600 watts and a peak power input of 1 kilowatt. The resulting heat load on the switch 158 would damage it and might lead to failure of the defibrillator 10.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

What is claimed is:

1. A defibrillator for supplying a defibrillator pulse comprising:
   a high voltage supply having a + terminal and a − terminal,
   a switch and an inductor in series between the high voltage supply and an output, said switch capable of being alternately connected between the positive and negative terminals of the high voltage supply many times during the defibrillator pulse,
   a sensor parallel with the inductor whose negative terminal is connected to a node between the switch and the inductor for measuring a physical parameter of the defibrillation output during the defibrillator pulse and
   control means responsive to the sensor output for controlling the alternate switching of the switch during the defibrillator pulse.

2. A defibrillator according to claim 1, wherein the sensor comprises a current sensing resistor coupled in series with the output.

3. A defibrillator according to claim 1, wherein the sensor comprises a voltage measurement device coupled across the terminals.

4. A defibrillator according to claim 1, wherein the high voltage supply comprises a capacitor bank.

5. A defibrillator according to claim 4, wherein the sensor comprises a voltage measurement device coupled across the terminals of the capacitor bank to measure delivered energy or power.

6. A defibrillator according to claim 1, where the control means comprises a negative feedback loop where the control signal representing the desired defibrillation waveform is compared to the above sensor signal and a comparison output is used to control the position of the switch.

7. A defibrillator according to claim 6, where the switch is connected to the negative terminal of the high voltage supply when the sensor signal is greater than the control signal times a first factor greater or equal to unity, and the switch is connected to the positive terminal of the high voltage supply when the sensor signal is less than the control signal times a second factor equal to or less than unity.

8. A defibrillator according to claims 2, 3, 4, or 7, where the desired current waveform increases from zero to a constant value of 2 to 15 amperes in 1 to 3 milliseconds, with a total duration of a first phase being 2 to 7 milliseconds, where the desired current waveform constant value is less for a second phase of the biphasic pulse.

9. A defibrillator according to claims 2, 3, 4, or 7, where the desired voltage waveform increases from zero to a constant value of 100 to 750 volts in 1 to 3 milliseconds, where the total duration of the first phase is 2 to 7 milliseconds, where the desired voltage waveform constant value is less for the second phase of the biphasic pulse.

10. A defibrillator according to claims 2, 3, 4, or 7, where the desired power waveform increases from zero to a constant value of 500 to 5000 watts in 1 to 3 milliseconds, where the total duration of the first phase is 2 to 7 milliseconds, where the desired power constant value is less for the second phase of the biphasic pulse.

11. A defibrillator according to claim 6, where the control signal has a constant value.

12. A defibrillator according to claim 6, where a value of the control signal starts at a zero value and increases during the first part of the waveform to a constant value for the remainder of the waveform.

13. A defibrillator according to claim 7, where the first factor is in the range of 1.0 to 1.2 and the second factor is in the range of 0.8 to 1.0: desired power wave form increases from zero to a constant value of 500 to 5000 watts in 1 to 3 milliseconds, where the total duration of the first phase is 2 to 7 milliseconds, where the desired power constant value is less for the second phase of the biphasic pulse.

14. A defibrillator according to claim 1, where the terminals are connected to a polarity-reversing double-throw double-pole switch to cause the defibrillator pulse to be a biphasic defibrillator pulse.

15. A defibrillator according to claims 14 or 12, where the desired control waveform changes to a different constant value corresponding to the second phase of the biphasic defibrillator pulse.

16. A defibrillator for supplying a defibrillator pulse comprising:
   a high voltage supply having a + terminal and a − terminal,
   a switch and an inductor in series between the high voltage supply and an output, said switch capable of being alternately connected between the positive and negative terminals of the high voltage supply many times during the defibrillator pulse,
   a sensor parallel with the inductor whose negative terminal is connected to a node between the switch and the inductor for measuring a physical parameter of the defibrillation output during the defibrillator pulse and
   control means responsive to the sensor output for controlling the alternate switching of the switch during the defibrillator pulse,
   wherein said sensor comprises a divider parallel with the inductor whose negative terminal is connected to a node between the switch and the inductor.

17. A defibrillator for providing a defibrillating current pulse to a heart, comprising:
- a high voltage generator for producing a high voltage potential;
- a low pass filter circuit coupled to the high voltage circuit for providing quasi-uniform defibrillating current pulse to a catheter;
- a sensor coupled and parallel with said high voltage generator for measuring a physical parameter of the high voltage potential produced by said high voltage generator; and
- a controller responsive to said sensor for controlling the current output from said low pass filter circuit providing the current supplied during the pulse to have a first polarity and a second polarity.

18. A defibrillator according to claim 17, wherein the low pass filter circuit comprises an inductor.

19. A defibrillator according to claim 18 wherein the controller comprises a microprocessor.

20. A defibrillator according to claim 17 wherein the high voltage generator comprises a high voltage capacitor.

21. A defibrillator according to claim 20 wherein the low pass filter comprises an inductor.

* * * * *